(12) United States Patent
Yoshida et al.

(10) Patent No.: US 9,380,999 B2
(45) Date of Patent: Jul. 5, 2016

(54) ULTRASONIC DIAGNOSTIC APPARATUS, ULTRASONIC IMAGE PROCESSING APPARATUS, AND MEDICAL DIAGNOSTIC IMAGING APPARATUS

(75) Inventors: Tetsuya Yoshida, Nasushiobara (JP); Itsuki Kuga, Nasushiobara (JP)

(73) Assignees: KABUSHIKI KAISHA TOSHIBA, Tokyo (JP); Toshiba Medical Systems Corporation, Otawara-shi (JP)

(*) Notice: Subject to any disclaimer, the term of this patent is extended or adjusted under 35 U.S.C. 154(b) by 31 days.

(21) Appl. No.: 13/074,459

(22) Filed: Mar. 29, 2011

(65) Prior Publication Data

US 2011/0245675 A1 Oct. 6, 2011

(30) Foreign Application Priority Data

Mar. 30, 2010 (JP) ................. 2010-078909

(51) Int. Cl.
*A61B 8/14* (2006.01)
*A61B 8/08* (2006.01)
(Continued)

(52) U.S. Cl.
CPC .............. *A61B 8/483* (2013.01); *A61B 8/461* (2013.01); *A61B 8/466* (2013.01); *A61B 8/481* (2013.01); *G01S 15/8979* (2013.01); *G01S 15/8993* (2013.01); *A61B 8/463* (2013.01); *G01S 7/52071* (2013.01)

(58) Field of Classification Search
CPC ........ A61B 8/461; A61B 8/463; A61B 8/466; A61B 8/481; A61B 8/483; G01S 7/52071; G01S 15/8979; G01S 15/8993
USPC ........................................................ 600/458
See application file for complete search history.

(56) References Cited

U.S. PATENT DOCUMENTS

| 6,505,064 B1* | 1/2003 | Liu et al. ........................ 600/420 |
| 2004/0096088 A1* | 5/2004 | Kohle ............................ 382/128 |

(Continued)

FOREIGN PATENT DOCUMENTS

| JP | 8-138077 A | 5/1996 |
| JP | 2714329 | 10/1997 |

(Continued)

OTHER PUBLICATIONS

Pratt, "Digital Image Processing". 4th edition. pp. 246-267. © Wiley-Interscience, John Wiley & Sons, Inc. Hoboken, New Jersey, 2007.*

(Continued)

*Primary Examiner* — Katherine Fernandez
*Assistant Examiner* — Colin T Sakamoto
(74) *Attorney, Agent, or Firm* — Oblon, McClelland, Maier & Neustadt, L.L.P.

(57) ABSTRACT

According to one embodiment, there is provided an ultrasonic diagnostic apparatus includes a data acquisition unit configured to scan a three-dimensional region in a subject having a contrast agent injected therein over a predetermined period by using ultrasonic waves and to thereby acquire ultrasonic data concerning the three-dimensional region over the predetermined period, a volume data generation unit configured to generate first volume data in each time phase in an analysis period by using the ultrasonic data concerning the three-dimensional region over the analysis period in the predetermined period and to generate second volume data indicative of contrast agent temporal information about the analysis period and third volume data indicative of a contrast agent characteristic amount at each position in the three-dimensional region in the analysis period, and an image generation unit configured to generate a projected image by using the second volume data and the third volume data.

19 Claims, 7 Drawing Sheets

(51) Int. Cl.
*A61B 8/00* (2006.01)
*G01S 15/89* (2006.01)
*G01S 7/52* (2006.01)

(56) References Cited

U.S. PATENT DOCUMENTS

| | | | |
|---|---|---|---|
| 2008/0081998 A1* | 4/2008 | Pan et al. | 600/458 |
| 2009/0015587 A1 | 1/2009 | Hashimoto et al. | |
| 2009/0124907 A1 | 5/2009 | Bruce et al. | |
| 2010/0053209 A1 | 3/2010 | Rauch et al. | |
| 2010/0094133 A1 | 4/2010 | Yoshiara et al. | |
| 2011/0015522 A1 | 1/2011 | Arditi et al. | |

FOREIGN PATENT DOCUMENTS

| | | |
|---|---|---|
| JP | 11-155858 | 6/1999 |
| JP | 2001-79003 A | 3/2001 |
| JP | 3495710 | 11/2003 |
| JP | 2004-321688 | 11/2004 |
| JP | 2007-111532 A | 5/2007 |
| JP | 2007-151881 | 6/2007 |
| JP | 2008-161675 | 7/2008 |
| JP | 2009-95671 A | 5/2009 |
| JP | 2010-240394 A | 10/2010 |
| WO | WO 2006/051831 A1 | 5/2006 |
| WO | WO 2006/090309 A2 | 8/2006 |
| WO | WO 2009/083557 A1 | 7/2009 |

OTHER PUBLICATIONS

Extended Search Report issued Jun. 29, 2011 in Europe Application No. 11160314.8.

Office Action issued Dec. 2, 2014 in Japanese Patent Application No. 2011-068899 (with English language translation).

* cited by examiner

ULTRASONIC DIAGNOSTIC APPARATUS, ULTRASONIC IMAGE PROCESSING APPARATUS, AND MEDICAL DIAGNOSTIC IMAGING APPARATUS

CROSS-REFERENCE TO RELATED APPLICATIONS

This application is based upon and claims the benefit of priority from Japanese Patent Application No. 2010-078909, filed Mar. 30, 2010; the entire contents of which are incorporated herein by reference.

FIELD

Embodiments described herein relate generally to an ultrasonic diagnostic apparatus, an ultrasonic image processing apparatus, and a medical diagnostic imaging apparatus.

BACKGROUND

The present embodiments relate to an ultrasonic diagnostic apparatus and others that can three-dimensionally visualize a temporal change in blood flow dynamic state in, e.g., an organ which is a diagnostic imaging target by using microbubbles as an ultrasonic contrast agent, and more particularly to an ultrasonic diagnostic apparatus, an ultrasonic image processing apparatus, and medical diagnostic imaging apparatus that can easily observe information of, e.g., a dynamic change in blood flow or fine angioarchitectonic with high visibility.

Ultrasonic diagnostic imaging is easy to use since a state of heartbeat or fetal movement can be obtained in real-time display by a simple operation, i.e., just applying an ultrasonic probe from a surface of a body, examinations can be repeatedly conducted because of high safety, a system scale is smaller than that of any other diagnostic device of X-ray, CT, or MRI, and bedside examinations can be also easily performed. Further, the ultrasonic diagnosis has no influence of radiation exposure as different from X-rays, and it can be used in obstetrics, home medical care, and others. Particularly, in recent years, an agitation probe (a probe that enables ultrasonic scan of a three-dimensional region by mechanically agitating a row of one-dimensionally aligned ultrasonic oscillators) or a two-dimensional array probe (a probe that enables ultrasonic scan of a three-dimensional region by a row of ultrasonic oscillators aligned in a matrix form) can be utilized to perform real-time three-dimensional scan (which is also called "four-dimensional scan").

Furthermore, in recent years, an intravenous administration type ultrasonic contrast agent has been productized. In the ultrasonic diagnostic imaging, performing contrast imaging using such a contrast agent enables acquiring various kinds of information. For example, in case of a primary liver cancer, a differential diagnosis about benign and malignancy and others can be carried out by complementarily using blood flow information of an arterial phase or blood flow information of a portal phase. Moreover, when the contrast imaging is performed after an RFA treatment, an ablated area is not stained, and hence this imaging is also applied to an effect judgment. Additionally, an imaging method for intravenously injecting an ultrasonic contrast agent to enhance a blood flow single in an examination of, e.g., a heart and a liver and thereby evaluating a blood flow dynamic state has been also suggested. A replenishment method and micro flow imaging are representative examples of an imaging method for evaluating the blood flow dynamic state.

The replenishment method is a technique by which characteristics that air bubbles of a contrast agent collapse are exploited, (a) a dynamic state of the air bubbles filling a scan cross section is observed under radiation of a low acoustic pressure, (b) the radiated acoustic pressure is switched to a high acoustic pressure to collapse the air bubbles in the cross section (in an irradiated volume in a precise sense), and (c) a state of the air bubbles that again flow into the cross section is observed.

In general, the contrast imaging is characterized in that a fine blood flow that cannot be visualized by, e.g., color Doppler can be visualized. On the other hand, only a small quantity of bubbles are present in the fine blood flow. Therefore, staining is non-steadily effected. The micro flow imaging is a technique that characteristics of such contrast imaging and a contrast agent are utilized and non-steadily visualized bubbles are temporally superimposed and displayed to more clearly visualize a fine blood flow configuration. When executing the micro flow imaging, there is a restriction that a patient must hold his/her breath for a fixed time and an examiner such as an operator must fix a probe. As a technology that alleviates this restriction, a technology that corrects movement of a target region by image processing has been also suggested (see, e.g., Patent Document 2).

In such contrast imaging, for example, dynamic information such as a staining start time phase (namely, which corresponds to a bubble arrival time), a time phase that staining achieves a peak (a peak time), a Wash-In time defined by an arrival time—a peak time of bubbles, a Wash-Out time defined by a time at which the bubbles flow out to a vein—the peak time is acquired spatially (i.e., at each position). It may be preferable for these pieces of dynamic information to be observed as moving images in some cases. For example, in case of a liver, a tumor is nourished with arterial blood, and a normal parenchyma is nourished with portal blood. Therefore, effecting observation using moving images enables putting a clock time that the contrast agent reaches a tumor region ahead of those in peripheral regions, thereby visually confirming how the tumor begins to be stained earlier than the other regions.

On the other hand, in the observation of moving images of the dynamic information, since a temporal change at each position must be retained in a user's head, it cannot be necessarily said that this observation is objective. Further, there is also a problem that the observation requires a certain amount of time. To solve these problems, a two-dimensional parametric imaging technology that enables observing dynamic information by using one two-dimensional image has been suggested. According to this technology, for example, a maximum value of a temporal change in luminance in each pixel is determined as a peak time, or a threshold value that is not affected by, e.g., noise is provided, a calculation of, e.g., determining a first time at which the threshold value is exceeded as an arrival time is performed to obtain temporal information. Furthermore, a two-dimensional image whose color tone is changed in accordance with each position is displayed based on a value of the obtained temporal information. It is effective to combine this technology with the above-described Micro Flow Imaging or movement correction technology, and utilization at clinical scenes in the future is expected.

However, in the two-dimensional parametric imaging, since two-dimensional image data (tomographic data) is used, there is a limit in representation of spatial continuity of a blood flow. It is difficult to recognize, e.g., a blood vessel having a configuration in a depth direction. For example, a blood vessel orthogonal to a tomographic image is substantially represented as a dot.

On the other hand, in case of observing a blood flow dynamic state (a temporal change in blood flow), when a plurality of pieces of volume data having different time phases are observed, the number of dimensions of the observation range increase by one as compared with a conventional diagnosis based on a two-dimensional image (a tomographic image), an observation time increases, and a problem that the construction (storage) of temporal change information also becomes ambiguous in an operator's head occurs.

Therefore, it can be considered that performing parametric imaging using time-series volume data (four-dimensional parametric imaging) is effective. However, in regard to three-dimensional visualizing method of temporal information such as an arrival time, a method that is effective in clinical practice has not been suggested. That is because simply three-dimensionally carrying out the two-dimensional parametric imaging cannot appropriately process temporal information concerning a depth direction. Particularly, in recent years, a contract imaging function has been introduced into ultrasonic diagnostic apparatuses that enable four-dimensional scan. Therefore, establishing a four-dimensional parametric imaging technique to enable three-dimensional observation of a dynamic blood flow state has a high clinical value and is strongly demanded.

In view of the above-described problems, it is an object of the present embodiment to provide an ultrasonic diagnostic apparatus, an ultrasonic image processing apparatus, and a medical diagnostic imaging apparatus that enable easily observing information such as a dynamic blood flow change or fine angioarchitectonic with high visibility based on the four-dimensional parametric imaging.

To achieve this object, the present embodiment takes the following measures.

In general, according to one embodiment, there is provided an ultrasonic diagnostic apparatus comprising: a data acquisition unit configured to scan a three-dimensional region in a subject having a contrast agent injected therein over a predetermined period by using ultrasonic waves and to thereby acquire ultrasonic data concerning the three-dimensional region over the predetermined period; a volume data generation unit configured to generate first volume data in each time phase in an analysis period by using the ultrasonic data concerning the three-dimensional region over the analysis period in the predetermined period and to generate second volume data indicative of contrast agent temporal information about the analysis period and third volume data indicative of a contrast agent characteristic amount at each position in the three-dimensional region in the analysis period; and an image generation unit configured to generate a projected image by using the second volume data and the third volume data.

DETAILED DESCRIPTION

Figure 1:
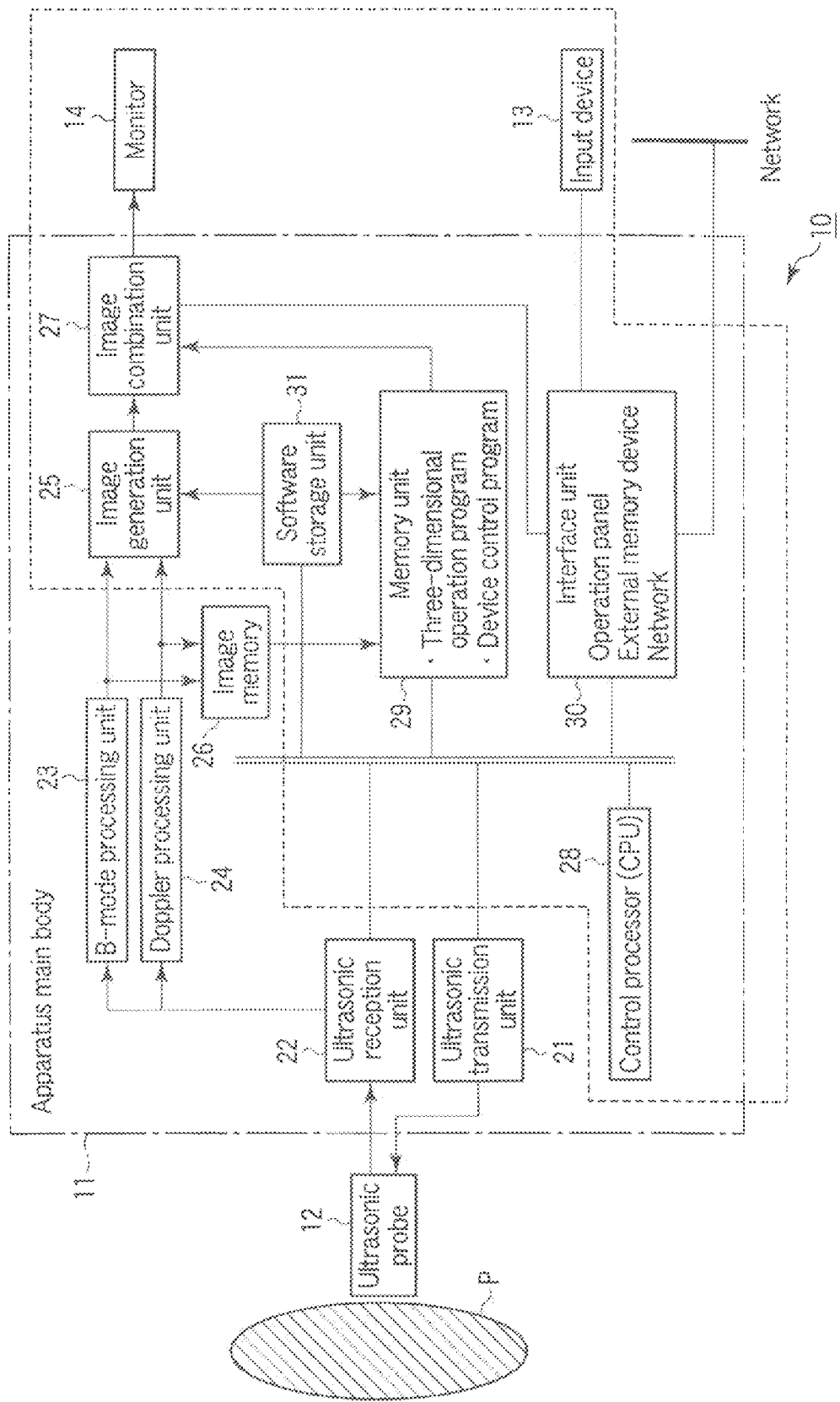
FIG. 1 is a block diagram of an ultrasonic diagnostic apparatus 1 according to this embodiment.

In general, according to one embodiment, there is provided an ultrasonic diagnostic apparatus comprising: a data acquisition unit that scans a three-dimensional region in a subject having a contrast agent injected therein by using ultrasonic waves over a predetermined period; a volume data generation unit that generates first volume data in each time phase in an analysis period by using ultrasonic data concerning the three-dimensional region over the analysis period in the predetermined period and also generate second volume data indicative of contrast agent temporal information about the analysis period and third volume data indicative of contrast agent temporal information about the analysis period and third volume data indicative of a contrast agent characteristic amount at each position in the three-dimensional region in the analysis period; and an image generation unit that generates a projected image by using the second volume data and the third volume data.

An embodiment according to the present embodiment will now be described hereinafter with reference to the drawings. It is to be noted that like reference numerals denote constituent elements having like functions and structures, and overlapping explanations will be given as required.

FIG. 1 is a block diagram of an ultrasonic diagnostic apparatus 1 according to this embodiment. As shown in the drawing, this ultrasonic diagnostic apparatus 10 comprises an ultrasonic probe 12, an input device 13, a monitor 14, an ultrasonic transmission unit 21, an ultrasonic reception unit 22, a B-mode processing unit 23, a Doppler processing unit 24, an image generation unit 25, an image memory 26, an image combination unit 27, a control processor (a CPU) 28, a memory unit 29, an interface unit 30, and a software storage unit 31. Although the ultrasonic transmission unit 21, the reception unit 22, and others built in an apparatus main body 11 may be constituted of hardware such as integrated circuits, they may be constituted of software programs that are formed as software modules in some cases. A function of each constituent element will now be described.

The ultrasonic probe 12 generates ultrasonic waves based on a drive signal from the ultrasonic transmission unit 21 and has a plurality of piezoelectric oscillators that convert a reflected wave from a subject into an electrical signal, a matching layer provided to the piezoelectric oscillators, a backing material that prevents the ultrasonic waves from the piezoelectric oscillators from being propagated toward the rear side, and others. When the ultrasonic waves are transmitted to the subject P from the ultrasonic probe 12, the transmitted ultrasonic waves are sequentially reflected on discontinuous surfaces having acoustic impedances of a body tissue and received by the ultrasonic probe 12 as echo signals. An amplitude of the echo signal is dependent on a difference between the acoustic impedances on the discontinuous surfaces on which the acoustic waves have been reflected. Moreover, echoes in a case that the transmitted ultrasonic pulses are reflected on a surface of a moving blood flow or a cardiac wall are dependent on a velocity component of a mobile object in an ultrasonic wave transmitting direction based on a Doppler effect and undergo frequency shift.

It is to be noted that the ultrasonic probe 12 included in this ultrasonic apparatus can perform ultrasonic scan with respect to a three-dimensional region of the subject. Therefore, the ultrasonic probe 12 has, e.g., a configuration that the oscillators are mechanically oscillated along a direction orthogonal to their alignment direction to scan a three-dimensional region by ultrasonic waves or a configuration that two-dimensionally aligned two-dimensional oscillation elements are utilized to scan a three-dimensional region by electrical control. When the former configuration is adopted, since the three-dimensional scan of the subject is performed by an oscillation circuit (an oscillation mechanism), a plurality of two-dimensional tomographic images can be automatically acquired by just bringing a probe main body into contact with the subject by an examiner. An accurate distance between cross sections can be also detected based on a controlled oscillation velocity. Additionally, when the latter configuration is adopted, a three-dimensional region can be scanned in principle by ultrasonic waves within a time equal to that required for obtaining two-dimensional tomographic images in a conventional example.

The input device 13 is connected with the apparatus main body 11 and has a track ball, various kinds of switches, a button, a mouse, a keyboard, and others that are used for fetching various kinds of instructions from an operator, conditions, an instruction to set a region of interest (ROI), various image quality condition setting instructions, and others into the apparatus main body 11.

The monitor 14 displays morphological information or blood flow information in the body as an image based on a video signal from the image combination unit 27 and others.

The ultrasonic transmission unit 21 has a trigger generation circuit, a delay circuit, and a pulsar circuit that are not illustrated. The pulsar circuit repeatedly generates a rate pulse used for forming a transmission ultrasonic wave at a predetermined rate frequency fr Hz (a cycle; 1/fr second). Further, the delay circuit supplies to each rate pulse a delay time required to converge ultrasonic waves in the form of a beam for each channel and determine transmission directional characteristics. Changing this delay information enables arbitrarily adjusting the transmitting direction from the probe oscillator surface. The trigger generation circuit applies a drive pulse to the probe 12 at a timing based on this rate pulse.

The ultrasonic reception unit 22 has an amplification circuit, an A/D converter, an adder, and others that are not illustrated. The amplification circuit amplifies an echo signal fetched through the probe 12 in accordance with each channel. The A/D converter provides the amplified echo signal with a delay time required to determine reception directional characteristics, and then the adder performs addition processing. A reflection component from a direction associated with the reception directional characteristics of the echo signal is enhanced by this addition, and a comprehensive beam for ultrasonic wave transmission and reception is formed based on the reception directional characteristic and the transmission directional characteristics.

The B-mode processing unit 23 receives the echo signal from the ultrasonic reception unit 22 and performs logarithm amplification, envelope detection processing, and others to generate data that a signal intensity is represented by brightness of luminance. At this time, a frequency band to be visualized can be changed by varying a detection frequency. Further, this unit is configured to enable performing respective types of detection processing based on two detection frequencies in parallel with respect to one piece of received data. When this configuration is utilized, a bubble image and a tissue image can be generated from one received signal. It is to be noted that, in case of visualizing bubbles, a second harmonic (a second-order harmonic) is mainly often visualized. Data subjected to processing in this B-mode processing unit 23 is output to the image generation unit 25 and reconfigured as a B-mode image that represents an intensity of a reflected wave as luminance.

The Doppler processing unit 24 carries out frequency analysis with respect to rate information from the echo signal received from the transmission/reception unit 22, extracts blood flow, tissue, and contrast agent echo components obtained by the Doppler effect, and thereby acquires blood flow information such as an average rate, a variance, power and others at multipoints. The acquired blood flow information is supplied to the image generation unit 24, and an average rate image, a variance image, a power image, and a combination image of these images can be displayed in the monitor 14 in colors.

The image generation unit 25 converts a scan line signal string for ultrasonic scan into a scan line signal string having a general video format as typified by a television and generates an ultrasonic diagnostic image as a display image. The image display unit 24 has a storage memory for storing image data mounted therein and, for example, an operator can call an image recorded during an examination after a diagnosis. Further, the image generation unit 25 has a function as an image processing device. For example, in case of configuring volume data, a scan line signal string obtained by performing ultrasonic scan with respect to a three-dimensional region or a continuous two-dimensional region is spatially arranged, and coordinate transformation, interpolation processing, and others are executed as required, thereby configuring volume data. The image generation unit 25 utilizes the obtained volume data to execute volume rendering, processing such as spatial MIP, MPR processing for an arbitrary tomographic image in the volume data based on cutout, micro flow imaging processing, movement correction processing, and others, thus generating a predetermined three-dimensional image. It is to be noted that various kinds of image processing methods and others in this image generation unit 25 may be any one of software techniques and hardware techniques.

Furthermore, the image generation unit 25 executes predetermined processing based on a later-described four-dimensional parametric imaging function under control of the control processor 28.

The image memory 26 temporarily stores ultrasonic data corresponding to a plurality of frames or a plurality of volumes.

The image combination unit 27 combines an image received from the image generation unit 25 with text information, a scale, and others as various parameters to be output to the monitor 14 as a video signal.

The control processor (a CPU) 28 has a function as an information processing device (a computer) and controls operations of this ultrasonic diagnostic apparatus main body. The control processor 28 reads a program for realizing various image processing methods and a program for realizing the later-described four-dimensional parametric imaging function from the memory unit 29, expands these programs on the software storage unit 31, and executes operations/controls and others concerning various kinds of processing.

The memory unit 29 stores programs for executing various scan sequences, a dedicated program for realizing the later-described four-dimensional parametric imaging function, a control program for executing image generation and display processing, diagnostic information (a patient ID, a physician's remarks, and others), a diagnostic protocol, transmission/reception conditions, a body mark generation program, and any other data groups. Further, the memory unit 29 is also used for storing images in the image memory 26 as required. The data in the memory unit 29 can be transferred to external peripheral devices through the interface unit 30.

The interface unit 30 is an interface concerning the input device 13, the network, and a new external memory device (not shown). The interface unit 30 can be utilized to transfer data such as an ultrasonic image, an analysis result, and others obtained by this device to other devices through the network.

(Four-Dimensional Parametric Imaging Function)

The four-dimensional parametric imaging function of this ultrasonic diagnostic apparatus 1 will now be described. According to this function, in the contrast imaging, first volume data that reflects a spatial density of a contrast agent (bubbles) in each time phase in a predetermined period as a signal value is generated by using ultrasonic data concerning the three-dimensional region over the predetermined period. Further, second volume data indicative of contrast agent temporal information at each position in the three-dimensional region and third volume data indicative of a contrast agent characteristic amount at each position in the three-dimensional region are generated by using the first volume data for each time phase in the predetermined period. Furthermore, the generated second volume data and third volume data are utilized to generate a three-dimensional image that the contrast agent characteristic amount at each position in the three-dimensional region is represented by a luminance value and the contrast agent temporal information is represented by a color tone, and the generated three-dimensional image is displayed in a predetermined conformation.

It is to be noted that, in the following explanation, a situation where the four-dimensional parametric imaging function is realized by using the ultrasonic diagnostic apparatus will be exemplified for a specific description. However, this function can be also realized by utilizing ultrasonic data acquired in advance by four-dimensional scan using, e.g., an ultrasonic image processing apparatus (or a viewer) based on a medical work station without being restricted to the above example. In such a case, a configuration within a dotted line in FIG. 1 can be adopted. Moreover, in any other medical diagnostic imaging apparatus using a contrast agent (e.g., an X-ray computerized tomography apparatus, a magnetic resonance imaging apparatus, or an X-ray diagnostic apparatus), for example, carrying out substantially the same configuration as that in the dotted line in FIG. 1 enables realizing the four-dimensional parametric imaging function.

Figure 2:
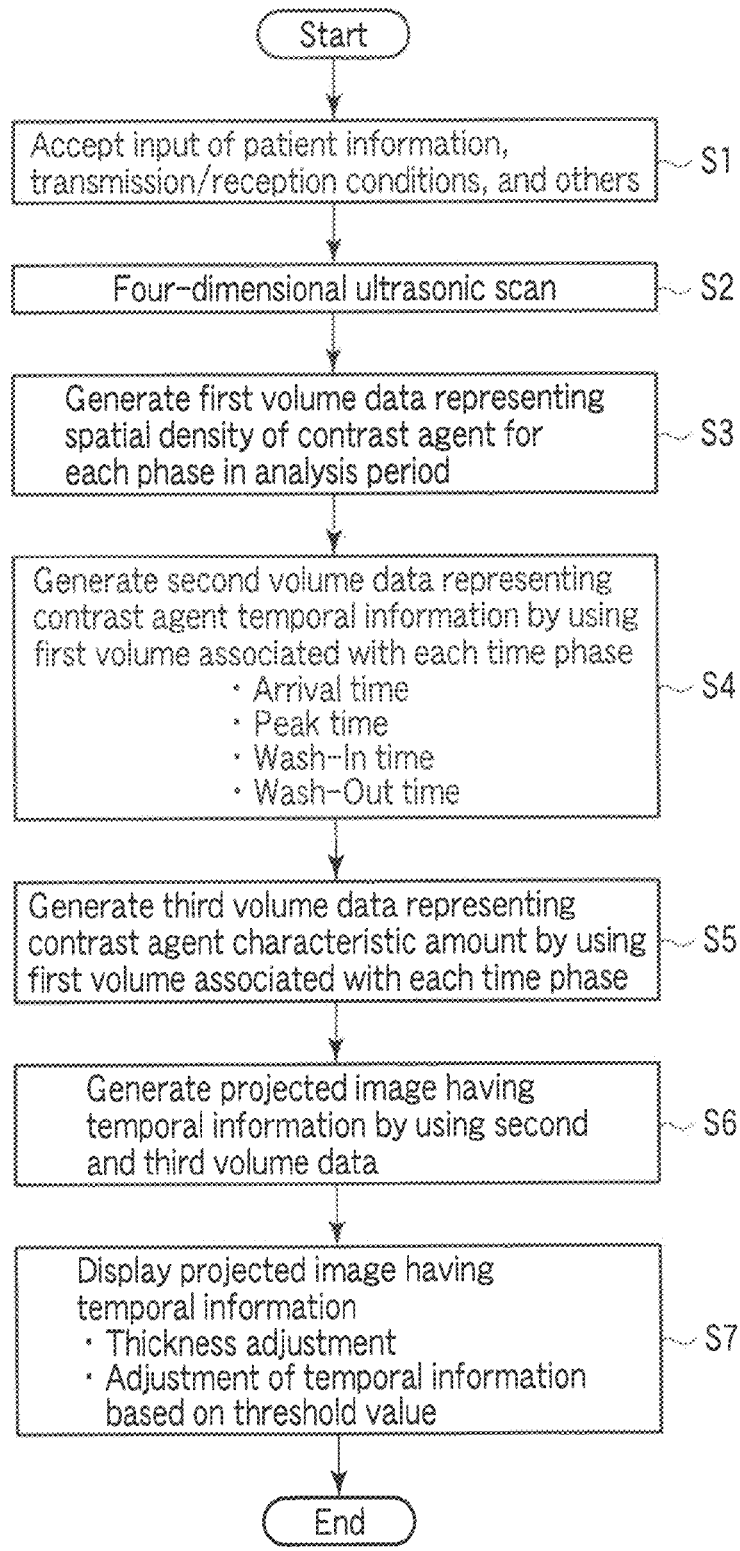
FIG. 2 is a flowchart showing a flow of processing based on this four-dimensional parametric imaging function (four-dimensional parametric imaging processing)

FIG. 2 is a flowchart showing a flow of processing conforming to this four-dimensional parametric imaging function (the four-dimensional parametric imaging processing). Contents of processing executed at each step shown in the flowchart will now be described.

[Input of Patient Information and Selection of Transmission/Reception Conditions, Scan Sequence, and Others: Step S1]

Input of patient information and selection of transmission/reception conditions (a field angle, a focal position, a transmission voltage, and others required to determine a size of a scan target region), a scan sequence for scanning a three-dimensional region of a subject by ultrasonic waves over a predetermined period, and others are executed through the operation unit 33 (a step S1). The input or selected various kinds of information/conditions and others are automatically stored in the memory device 29.

[Collection of Volume Data Over Predetermined Period: Step S2]

Then, the transmission/reception control unit 31 determines a three-dimensional region including a predetermined region of a subject (e.g., a blood vessel as a diagnostic target) as a scan target region and executes real-time three-dimensional ultrasonic scan (four-dimensional scan) over a predetermined period to obtain three-dimensional ultrasonic data associated with each time phase in the predetermined period (a step S2).

[Generation of First Volume Data Representing Spatial Density of Contrast Agent: Step S3]

Figure 3:
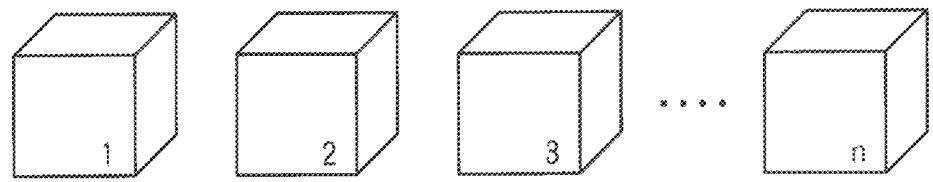
FIG. 3 is a view conceptually showing first volume data associated with each time phase k (k=1, 2, . . . , n) in a predetermined period.

Subsequently, the image generation unit 25 executes extraction processing for a harmonic component associated with a signal component from the contrast agent, coordinate transformation, interpolation processing, and others with respect to the acquired three-dimensional ultrasonic data to generate first volume data associated with each of such time phases k (k=1, 2, ..., n) as shown in FIG. 3 (a step S3). In this first volume data, a spatial density (a concentration) of the contrast agent at each time phase is represented by a signal value (a luminance value). Therefore, analyzing the time-series first volume data enables grasping a temporal change in contrast agent density at each position in the three-dimensional region which is a scan target region.

[Generation of Second Volume Data Representing Temporal Information Concerning Contrast Agent: Step S4]

Then, the image generation unit 25 utilizes the first volume data for each time phase associated with an analysis period (a period that is an analysis target of the four-dimensional parametric imaging in a predetermined period) in the first volume data over the predetermined period to generate second volume data indicative of temporal information concerning the contrast agent (a step S4). Here, the temporal information concerning the contrast agent is, e.g., an arrival time of the contrast agent at each position, a peak time of a signal value (or a luminance value), a Wash-In time, or a Wash-Out time.

It is to be noted that a start time and an end time of the analysis period can be arbitrarily set by an operation from the input device 13. Further, for example, an ON time of a contrast agent timer, an end time of a burst that destroys bubbles, a time at which bubbles entered (reached) a given target, and others may be detected, and the apparatus may automatically start the analysis period, for example.

Furthermore, it is assumed that the second volume data is created to be equal to the plurality of first volume data associated with the analysis time in number (in conformity to a time phase of each first volume). However, the present embodiment is not restricted thereto, and the second volume data may be single volume data, for example. The second volume data generated at this step will now be described in accordance with each type of contrast agent temporal information.

(In Case of Determining Contrast Agent Temporal Information as Arrival Time of Contrast Agent)

The image generation unit 25 first utilizes the plurality of pieces of first volume data associated with the respective time phases in the analysis period to generate a TIC (Time Intensity Curve) in the analysis period about each voxel.

Figure 4:
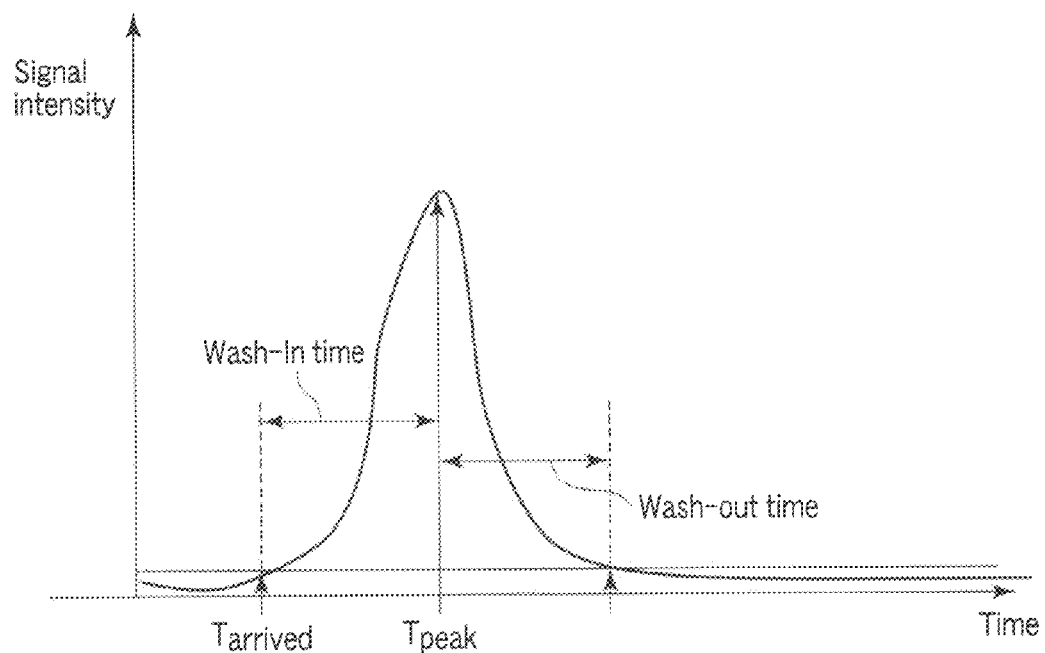
FIG. 4 is a view showing an example of a TIC in an analysis period of a given voxel.

FIG. 4 is a view showing an example of the TIC in the analysis period about a given voxel. The image generation unit 25 utilizes the TIC in the analysis period about each generated voxel to observe a temporal change in luminance of each voxel and calculates a first time $T_{arrived}$ at which such a preset luminance threshold value as shown in FIG. 4 is exceeded in accordance with each voxel by using a volume rate and a volume number. When this calculated time is determined as a voxel value, the second volume data can be calculated.

Furthermore, in regard to the first volume data associated with a first time phase in the analysis period, a voxel value of a voxel whose luminance value exceeds the threshold value from the beginning may be determined as zero or no value. That is because a luminance value of such voxel often arises from a signal from a tissue rather than a signal from bubbles.

When the contrast agent temporal information is an arrival time of the contrast agent in this manner, the same number of pieces of second volume data as the plurality of pieces of first volume data associated with the analysis period may be created. However, for example, if the single second volume data associated with a last time phase in the analysis period is present, the contrast agent arrival time in the analysis period about each voxel can be grasped.

(In Case of Determining Contrast Agent Temporal Information as Peak Time that Luminance Value Reaches Peak)

The image generation unit 25 first utilizes the plurality of pieces of first volume data associated with the respective time phases in the analysis period to generate a TIC (Time Intensity Curve) in the analysis period about each voxel. Then, the image generation unit 25 observes a temporal change in luminance of each voxel by using the TIC in the analysis period about each generated voxel and calculates a time $T_{peak}$, at which a luminance value becomes maximum (a peak) as shown as shown in FIG. 4, in accordance with each voxel. When this calculated time is determined as a voxel value, the second volume data can be generated.

Figure 5:
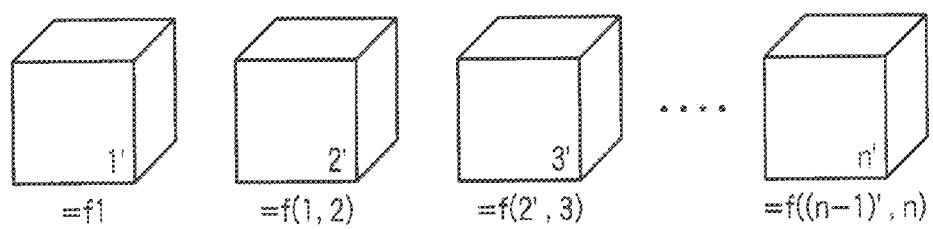
FIG. 5 is a view for explaining second volume data generation processing using the plurality of pieces of first volume data associated with respective time phases in the analysis period.
Figure 6:
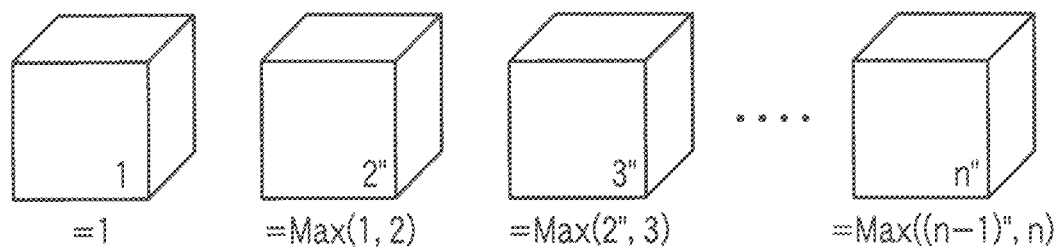
FIG. 6 is a view for explaining third volume data generation processing using the plurality of pieces of first volume data associated with the respective time phases in the analysis period.

Even in a situation that the temporal information concerning the contrast agent is the peak time at which the luminance value achieves a peak in this manner, the same number of pieces of second volume data as the plurality of pieces of first volume data associated with the analysis period may be created. However, the arrival time is not updated when it is once obtained. On the other hand, in case of the peak time, for example, as shown in FIG. 5, a magnitude comparison operation f(k−1, k) (where k=1, 2, . . . , n) of luminance values is executed between volumes adjacent to each other in time series, and the temporal information is also updated every time the luminance exceeds a past maximum value. In a strict sense, when observing the luminance until it achieves a peak and Wash-Out is realized, the number of peak time should be one in each voxel. Therefore, for example, if the number of second volume associated with the last time phase in the analysis period is one, an arrival time of the contrast agent in the analysis period can be grasped with respect to each voxel.

(In Case of Determining Contrast Agent Temporal Information is Wash-In Time of Contrast Agent)

As shown in FIG. 4, the Wash-In time is defined as, e.g., a peak time—an arrival time. In such a case, a temporal change in luminance of each voxel can be observed by using the TIC about the analysis time, and a time at which the luminance value exceeds a given threshold value (the arrival time) and a time at which the luminance becomes maximum (the peak) can be specified in accordance with each voxel to calculate the Wash-In time with respect to each voxel. When this calculated time (period) is determined as a voxel value, the second volume data when the temporal information concerning the contrast agent is determined as the Wash-In time of the contrast agent can be generated as, e.g., a single volume.

(In Case of Determining Temporal Information Concerning Contrast Agent as Wash-Out Time)

As shown in FIG. 4, the Wash-Out time is defined as a period form a time at which a peak is once achieved (the peak time) to a time at which the TIC is reduced to a predetermined threshold value or below. It is to be noted that fitting or smoothing the TIC in advance is preferable. In such a case, a temporal change in luminance in each voxel is observed by using the TIC in the analysis period, and a period from a time at which the luminance value becomes maximum (the peak) to a time at which it becomes the predetermined threshold value or below is calculated in accordance with each voxel. When this calculated time (period) is determined as a voxel value, the second volume data when the temporal information concerning the contrast agent is the Wash-Out time of the contrast agent can be generated as, e.g., a single volume.

It is to be noted that the generation of the second volume data concerning the various kinds of temporal information about the contrast agent is processing presupposing that the same voxel is placed at the same position. However, in reality, no matter how firmly the probe is held, a hand may be moved, or the probe may be moved due to a patient's breathing, and complexly fixing the probe is difficult. Thus, for example, correcting a displacement between continuous volumes by an apparatus that adopts a movement correction technology disclosed in JP-A 2007-330764 (KOKAI) is very useful when utilizing this suggested technique in an actual examination.

[Generation of Third Volume Data Representing Contrast Agent Characteristic Amount at Each Position: Step S5]

Then, the image generation unit 25 utilizes the first volume data for each time phase associated with the analysis period to generate third volume data representing a contrast agent characteristic amount in the analysis period in accordance with each position in the scan target region (a step S5). Here, the contrast agent characteristic amount in the analysis period is, e.g., a maximum value, a minimum value, or an average value of a signal value (a luminance value) at each position in the analysis period.

For example, it is assumed that a maximum value of a signal value (a luminance value) is used as the contrast agent characteristic amount in the analysis period to trace bubbles for vascular morphology observation. In such a case, the image generation unit 25 generates third volume data by utilizing the first volume data for each time phase associated with the analysis period to carry out temporal maxhold in a time direction with respect to each voxel associated with a spatial position (for example, by sequentially executing a maximum value (magnitude) comparison operation Max(k−1, k) (where k=1, 2, . . . , n) of luminance values between volumes adjacent to each other in time series as shown in FIG.

6 and updating the temporal information every time the luminance exceeds a past maximum value).

It is to be noted that, when the maximum value of the signal value (the luminance value) is used in this manner, the third volume data may be single data associated with a last time phase in the analysis period. However, when the final single data alone is adopted, a tumor vessel/arterial vessel stained on the earliest stage is embedded in a perfusion stained on the latest stage, the blood vessel may be possibly hard to see. Therefore, it is preferable to create the same number of pieces of third volume data as the plurality of pieces of first volume data associated with the respective time phases in the analysis period.

[Generation of Projected Image Using Second and Third Volume Data: Step S6]

Then, the image generation unit 25 generates a projection image by using the second and the third volume data (Step S6).

Figure 7:
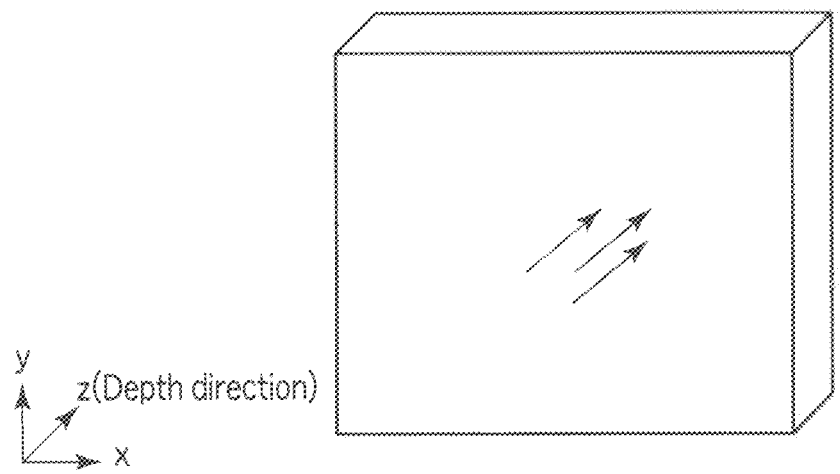
FIG. 7 is a view for explaining projection processing using second and third volume data.
Figure 8:
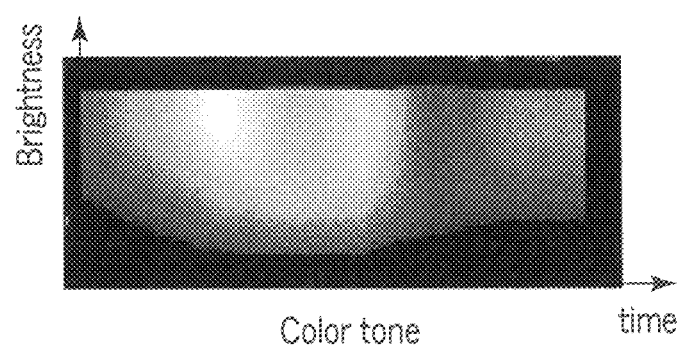
FIG. 8 is a view showing an example of a color map used for generation of a projected image using the second and third volume data.

FIG. 7 shows a view for explaining projection processing using the second and the third volume data. FIG. 8 is a view showing an example of a color map used in the projection processing. The color map assigns different color tone to each pixel according to time and pixel values (brightness) of each pixel.

Then, the image generation unit 25 executes projection processing determining the depth direction as an eye direction as show in FIG. 7 with respect to the third volume data in accordance with each ray and selects a color tone associated with the contrast agent temporal information in accordance with each position by using the second volume data and a color map shown in FIG. 8, thereby generating a projected image (a four-dimensional parametric image) that the contrast agent characteristic amount at each position in the three-dimensional region is represented as a luminance value and the contrast agent temporal information is represented as a color tone (a step S6).

Here, in a projection range, a plurality of pieces of temporal information are present in each eye direction (i.e., in accordance with each ray) (in other words, information concerning the depth direction is added). Such assignment of a color phase associated with the temporal information concerning the contrast agent can be represented by any one of the following techniques according to the embodiment.

(Variance Value Display)

A technique according to this embodiment utilizes variance values to express the plurality of pieces of temporal information present along the eye direction. For example, in a region where blood vessels of a tumor and the like are complicated, the temporal information has a large variance in the depth direction. On the other hand, in a region that mainly consists of capillary blood vessels (perfusions) without large blood vessels, the temporal information has a small variance. That is, for example, whether staining is even or uneven or whether a large quantity of blood vessels and the like are contained can be expressed by changing a color in accordance with a variance.

Figure 9:
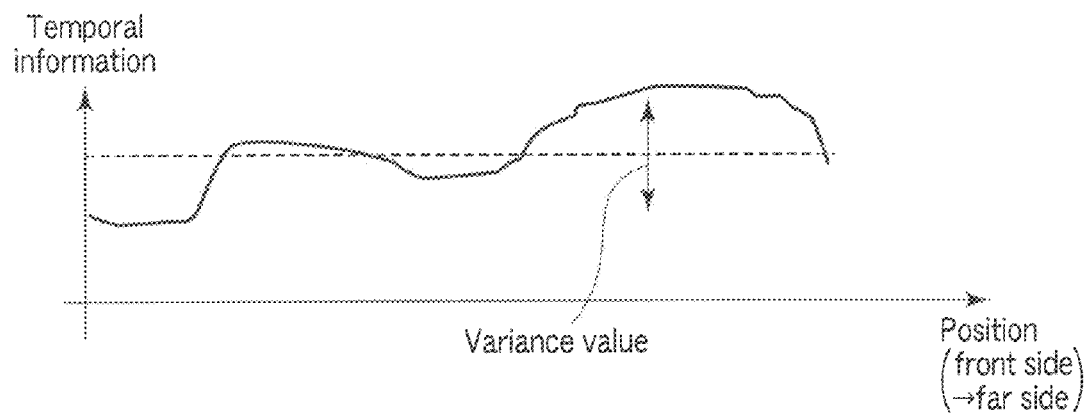
FIG. 9 is a view for explaining assignment processing concerning a depth direction of contract agent temporal information.

FIG. 9 is a graph obtained by plotting a voxel value of the second volume data present on a given ray from a front side toward a far side of an observing point. In this embodiment, as shown in FIG. 9, the image generation unit 25 calculates a variance of the voxel value of the voxel in the second volume data in accordance with each ray and assigns a color tone associated with the obtained variance value.

It is to be noted that, for example, when another internal organ enters the depth range, the variance value is considered to unnecessarily increase. Therefore, it can be said that setting the projection range is important. Optimization of the projection range can be realized by a later-described technique.

(Average Value Display)

A technique according to this embodiment expresses the plurality of pieces of temporal information present along the eye direction by using an average value. That is, the image generation unit 25 calculates an average value of voxel values of voxels in the second volume data in accordance with each ray and assigns luminance associated with the obtained average value.

(Arrival Time Display)

Figure 10:
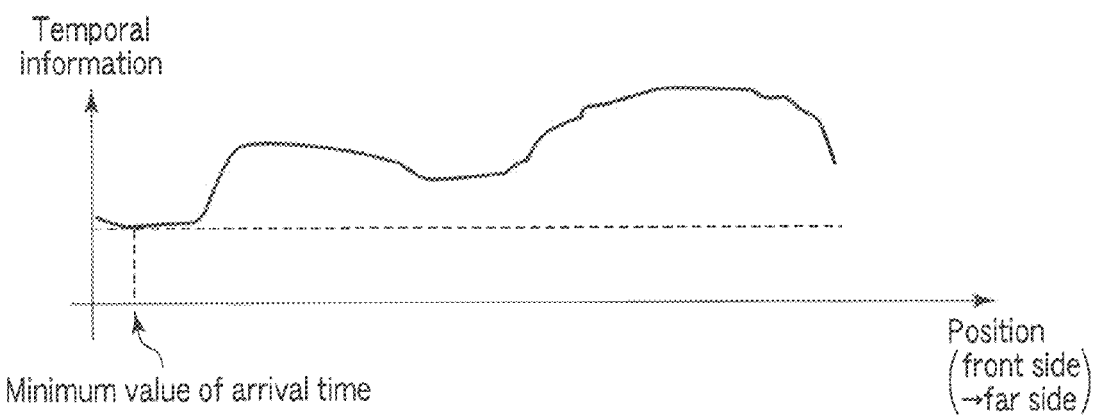
FIG. 10 is a view for explaining the assignment processing concerning the depth direction of the contrast agent temporal information.

A technique according to this embodiment expresses the plurality of pieces of temporal information present in the eye direction with an arrival time being determined as a reference. For example, as shown in FIG. 10, the image generation unit 25 searches for a voxel whose arrival time is a minimum value (however, one having the temporal information=0 is excluded), determines a color tone based on this arrival time, and determines a luminance value at a position associated with this voxel by using the first volume data to execute the projection professing.

(Peak Time Display)

Figure 11:
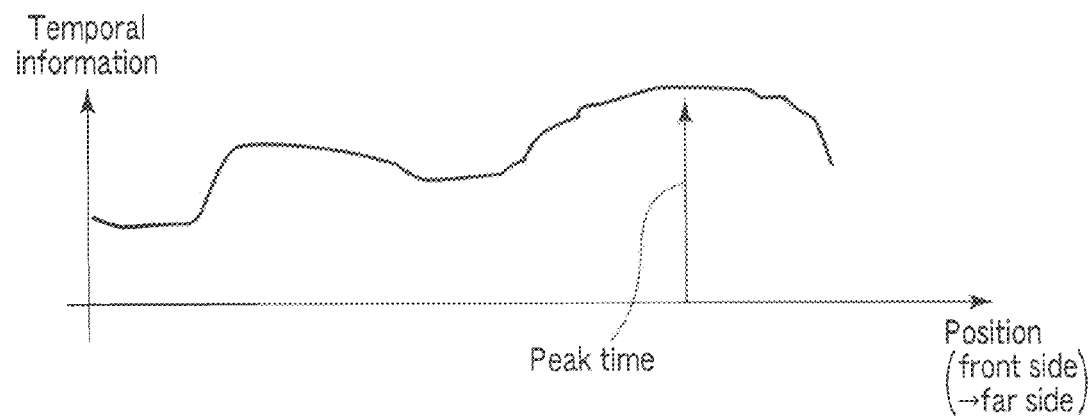
FIG. 11 is a view for explaining the assignment processing concerning the depth direction of the contrast agent temporal information.

A technique according to this embodiment expresses the plurality of pieces of temporal information present in the eye direction with a peak time (a maximum value) being determined as a reference. For example, as shown in FIG. 11, the image generation unit 25 searches for a voxel having a peak time, determines a color tone based on an arrival time of this voxel, and determines a luminance value at a position associated with this voxel by using the first volume data, thereby executing the projection processing. It is to be noted that, when a plurality of peak times are present, a high priority is put on information of a voxel placed on the front side.

(Others)

Additionally, besides the respective foregoing embodiments, for example, a voxel having a maximum luminance value (or a voxel having a minimum luminance value) in the depth direction can be specified in the third volume data, and a color tone can be selected by using the temporal information of a voxel in the second volume associated with a position of the former voxel.

[Display of Projected Image: Step S7]

The generated projected image is combined with predetermined text information and others by the image combination unit 27 and displayed in a predetermined conformation in the monitor 14.

Modifications of this four-dimensional parametric imaging will now be described.

Modification 1

In this four-dimensional parametric imaging, a thickness of data in the depth direction (a projection range) as a projection processing target can be adjusted in the projection processing of the step S6. For example, a desired tomographic image is displayed in response to an instruction from a user. The image generation unit 25 determines the displayed tomographic image as a reference and specifies a thickness concerning the depth direction (the projection range). For example, the image generation unit 25 specifies a predetermined range with the tomographic image displayed in the depth direction at the center, a predetermined range extending toward a far side of screen from the displayed tomographic image, or a predetermined range extending toward a front side of the screen from the displayed tomographic image. It is to be noted that this projection range can be arbitrarily adjusted by a manual operation from an operator.

Based on such a configuration, when the projection range can be set, a user can very easily set an observation range, and the connection between depicted blood vessels can be improved by increasing the thickness. In case of adopting the variance display in the projection processing in particular, for example, when another organ enters the depth range, a variance value unnecessarily increases. Therefore, accurately setting the projection range by using this technique is effective.

Modification 2

In this four-dimensional parametric imaging, a voxel as a projection processing target can be selected (changed/adjusted) in accordance with the contrast agent information in the projection processing of the step S6. For example, when threshold processing is carried out with respect to the second volume data, a voxel that is early or late in terms of the contrast agent temporal information can be selectively displayed. For example, a predetermined threshold value can be provided to the contrast agent temporal information in response to an instruction from the user, and each unnecessary voxel can be excluded by the threshold processing using the provided value, thereby projecting and displaying the second volume data.

Modification 3

In this four-dimensional parametric imaging, a plurality of thicknesses of data in the depth direction (a projection range) as a projection processing target can be set to cover the entire ranges of the first, second, and third volume data in the projection processing of the step S6.

Figure 12:
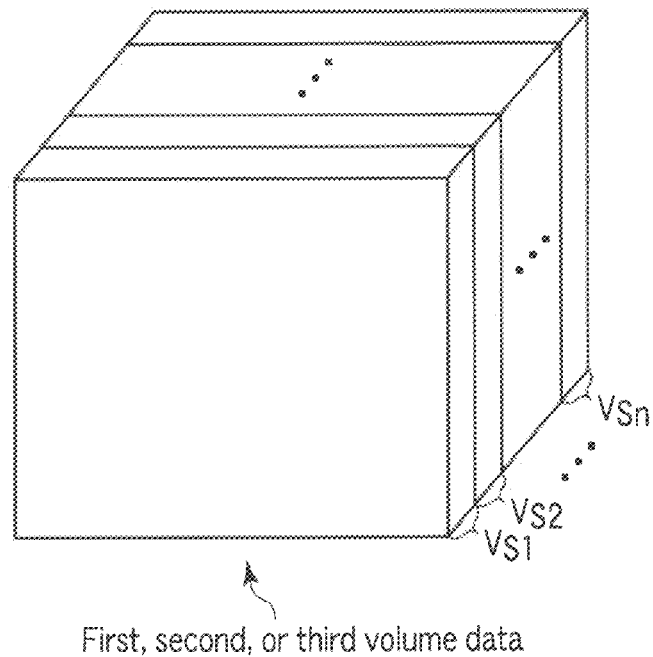
FIG. 12 is a view for explaining an example when the first, second, or third volume data is divided to generate a plurality of projection regions.

For example, each piece of first, second, and third volume data is divided into pieces of sub-volume data Vs1 to Vsn having the same width in the depth direction as shown in FIG. 12, each sub-volume data is determined as the projection range, and the projection processing of the step S6 is executed. A division width of the sub-volume can be arbitrarily set by a manual operation from the operator.

Figure 13:
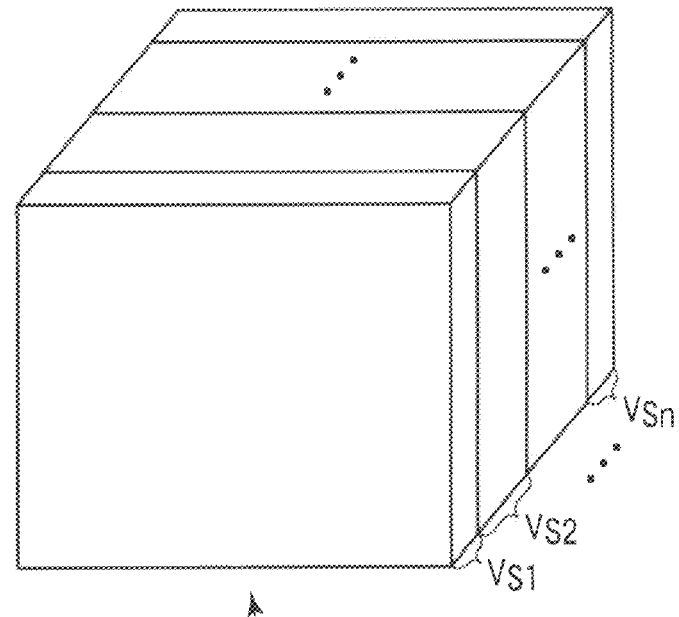
FIG. 13 is a view for explaining another example when the first, second, or third volume data is divided to generate a plurality of projection regions.

Further, each piece of first, second, and third volume data is divided into pieces of sub-volume data Vs1 to Vsn having respective arbitrary widths in the depth direction as shown in FIG. 13, each sub-volume data is determined as the projection range, and the projection processing of the step S6 is executed. The widths of the respective sub-volumes can be arbitrarily set by a manual operation from the operator.

Figure 14:
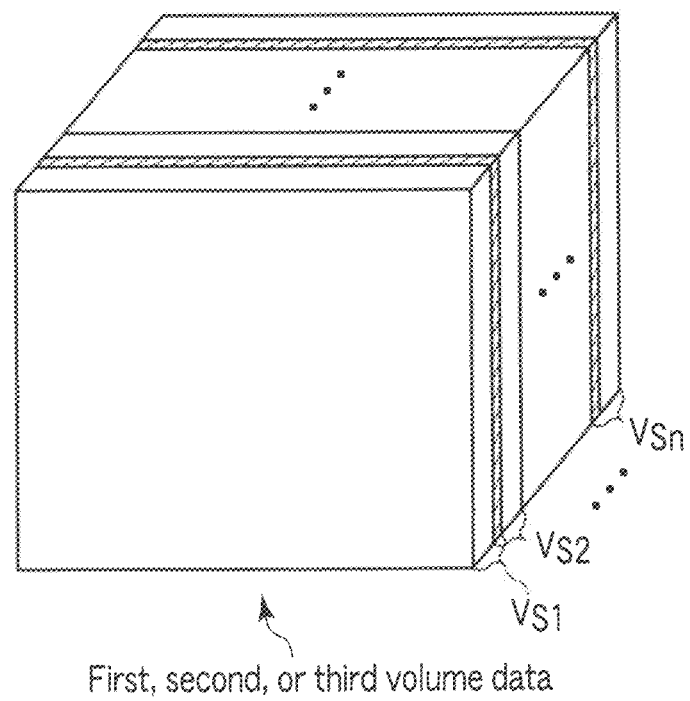
FIG. 14 is a view for explaining still another example when the first, second, or third volume data is divided to generate a plurality of projection regions.

Furthermore, each piece of first, second, and third volume data is divided into pieces of sub-volume data Vs1 to Vsn that partially overlap in the depth direction as shown in FIG. 14, each sub-volume data is determined as the projection range, and the projection processing of the step S6 is carried out. It is to be noted that each shaded area in the drawing represents an overlap region of the sub-volumes adjacent to each other. An overlap width can be arbitrarily set by a manual operation from the operator.

In such cases, projected images, whose number is associated with the respective sub-volumes, are generated. Therefore, at a step S7, each projected image associated with each sub-volume is individually displayed or displayed in a multi-view mode.

Based on such a configuration, the entire pieces of first, second, and third volume data can be visualized. Therefore, visualization can be carried out based on the four-dimensional parametric imaging without missing a region beneficial to an image diagnosis.

(Effect)

According to the above-described configuration, in the contrast imaging, the ultrasonic data concerning the three-dimensional region over a predetermined period is utilized to generate the first volume data reflecting a spatial density of the contrast agent (bubbles) in each time phase in the predetermined period. Furthermore, the second volume data representing the contrast agent temporal information at each position in the three-dimensional region and the third volume data representing the contrast agent characteristic amount at each position in the three-dimensional region are generated by using the first volume data for each time phase in the predetermined period. Moreover, the generated second volume data and third volume data are utilized to generate a three-dimensional image that the contrast agent characteristic amount at each position in the three-dimensional region is represented by a luminance value and the contrast agent temporal information is represented by a color tone, and the generated image is displayed in a predetermine conformation. Therefore, the temporal information concerning the depth direction can be appropriately processed, and information such as a dynamic blood flow change or fine angioarchitectonic can be easily observed with high visibility.

Additionally, in regard to the temporal information, an arrival time, a peak time, a Wash-In time, or a Wash-Out time can be selected as required. Further, as to the projection technique, a variance value or an arrival time can be selected as reference if need arises. Therefore, a user can set desired parameters in accordance with each situation, thereby realizing the four-dimensional parametric imaging with a high freedom degree. Further, for example, when the projection range is adjusted to prevent other ranges from entering, the preferred embodiment can be realized.

It is to be noted that the present embodiment is not restricted to the foregoing embodiments as they are, and it can be embodied by modifying constituent elements without departing from the gist of the embodiment on the embodying stage. For example, there are the following specific modifications.

(1) Each function according to this embodiment can be also realized by installing programs executing the processing in a computer such as a workstation and expanding these programs on the memory. At this time, the program that can allow the computer to execute the technique can be stored in a recording medium such as a magnetic disk (a floppy (a registered trademark) disk or a hard disk), an optical disk (a CD-ROM or a DVD), a semiconductor memory, and others so that the program can be distributed in the stored state.

(2) In the foregoing embodiment, the example where the volume data consisting of the voxel data is utilized to execute the four-dimensional parametric imaging processing has been described. However, volume data consisting of raw data may be utilized to execute the four-dimensional parametric imaging processing without being restricted to the above example.

Further, appropriately combining a plurality of constituent elements disclosed in the foregoing embodiment enables forming various kinds of inventions. For example, some of all the constituent elements disclosed in the embodiment may be deleted. Furthermore, constituent elements in different embodiments may be appropriately combined.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an ultrasonic probe configured to acquire ultrasonic data of a three-dimensional region in a subject having a contrast agent injected therein over a predetermined period by scanning the three-dimensional region with ultrasonic waves over the predetermined period; and
a computer configured, via programs stored on a non-transitory computer-readable medium, to:
generate first volume data in each time phase in an analysis period by using the acquired ultrasonic data concerning the three-dimensional region over the analysis period in the predetermined period and to generate second volume data indicative of contrast agent temporal information about the analysis period and third volume data indicative of a contrast agent characteristic amount at each position in the three-dimensional region in the analysis period, the second volume data and the third volume data being generated from the first volume data, wherein the contrast agent temporal information in the second volume data is one of a contrast agent arrival time for each voxel in the second volume data, a peak time at which a luminance value of the first volume data becomes a maximum value, a Wash-In time, and a Wash-Out time, and the contrast agent characteristic amount is one of a maximum value of the luminance value, a minimum value of the luminance value, and an average value of the luminance value;
determine a display color for each pixel in a projected image of the second volume data and the third volume data by
assigning, to each position in the three-dimensional region by use of a color map, a color phase and a display attribute different from the color phase associated with the contrast agent temporal information and the contrast agent characteristic amount of each position respectively,
determining a projection direction,
determining, for each pixel in the projected image, a ray along the projection direction and identifying assignment results having positions that intersect the ray,
projecting, for each pixel in the projected image, the identified assignment result along the ray, and
determining a display color for each pixel based on the respective projections of the identified assignment results along respective rays; and
generate the projected image using the determined display colors.

2. The apparatus according to claim 1, wherein the computer is further configured to:
calculate, for each ray of its respective projected image pixel, one of a variance value of the contrast agent temporal information having positions that intersect with the ray, a maximum value of the contrast agent temporal information having positions that intersect with the ray, a minimum value of the contrast agent temporal information having positions that intersect with the ray, and an average value of the contrast agent temporal information having positions that intersect with the ray by using the second volume data, and
generate the projected image using the color map by assigning, to each pixel of the projection image, a color phase that differs depending on the respective value.

3. The apparatus according to claim 1, wherein the computer is further configured to:
select, from the voxels of the third volume data intersected by each respective ray, a voxel having a maximum or minimum luminance value for each respective ray,
specify a voxel in the second volume data associated with the selected voxel for each selected voxel respectively, and
assign color phases to respective projected image pixels associated with respective rays that differ depending on respective contrast agent temporal information of the specified voxels.

4. The apparatus according to claim 1, wherein the computer is further configured to calculate:
a temporal change in luminance value at each position in the three-dimensional region by using the first volume data in each time phase in the analysis period, and
one of the peak time, the Wash-In time, and the Wash-Out time by using the temporal change in the luminance value at each position in the three-dimensional region.

5. The apparatus according to claim 1, wherein the computer is further configured to:
set at least one projection range that is used when generating the projected image, and
utilize the at least one set projection range to generate the at least one projected image.

6. The apparatus according to claim 5, further comprising a display configured to perform, when a plurality of the projected images has been generated, a multi-view display of the plurality of projected images.

7. An ultrasonic image processing apparatus, comprising:
an ultrasonic probe configured to acquire ultrasonic data concerning a three-dimensional region in a subject having a contrast agent injected therein, by scanning the three-dimensional region with ultrasonic waves over the predetermined period by using the ultrasonic probe;
a memory configured to receive and store ultrasonic data concerning the three-dimensional region, from the ultrasonic probe; and
a computer configured, via programs stored on a non-transitory computer-readable medium, to:
generate first volume data in each time phase in an analysis period by using the ultrasonic data concerning the three-dimensional region over the analysis period in the predetermined period and to generate second volume data indicative of contrast agent temporal information about the analysis period and third volume data indicative of a contrast agent characteristic amount at each position in the three-dimensional region in the analysis period, the second volume data and the third volume data being generated from the first volume data, wherein the contrast agent temporal information in the second volume data in one of a contrast agent arrival time for each voxel in the second volume data, a peak time at which a luminance value of the first volume data becomes a maximum value, a Wash-In time, and a Wash-Out time, and the contrast agent characteristic amount is one of a maximum value of the luminance value, a minimum value of the luminance value, and an average value of the luminance value;
determine a display color for each pixel in a projected image of the second volume data and the third volume data by:

assigning, to each position in the three-dimensional region by use of a color map, a color phase and a display attribute different from the color phase associated with the contrast agent temporal information and the contrast agent characteristic amount of each position respectively, determining a projection direction, determining, for each pixel in the projected image, a ray along the projection direction and identifying assignment results having positions that intersect the ray, projecting, for each pixel in the projected image, the identified assignment result along the ray, and determining a display color for each pixel based on the respective projections of the identified assignment results along respective rays; and generate the projected image using the determined display colors.

8. The apparatus according to claim 7, wherein the computer is further configured to:

calculate, for each ray of its respective projected image pixel, one of a variance value of the contrast agent temporal information having positions that intersect with the ray, a maximum value of the contrast agent temporal information having positions that intersect with the ray, a minimum value of the contrast agent temporal information having positions that intersect with the ray, and an average value of the contrast agent temporal information having positions that intersect with the ray by using the second volume data, and generate the projected image using the color map by assigning, to each pixel of the projection image, a color phase that differs depending on the respective calculated value.

9. The apparatus according to claim 7, wherein the computer is further configured to:

select, from the voxels of the third volume data intersected by each respective ray, a voxel having a maximum or minimum luminance value for each respective ray, specify a voxel in the second volume data associated with the selected voxel for each selected voxel respectively, and assign color phases to respective projected image pixels associated with respective rays that differ depending on respective contrast agent temporal information of the specified voxels.

10. The apparatus according to claim 7, wherein the computer is further configured to calculate:

a temporal change in luminance value at each position in the three-dimensional region by using the first volume data in each time phase in the analysis period, and one of the peak time, the Wash-In time, and the Wash-Out time by using the temporal change in the luminance value at each position in the three-dimensional region.

11. The apparatus according to claim 7, wherein the computer is further configured to:

set at least one projection range that is used when generating the projected image, and utilize the at least one set projection range to generate the at least one projected image.

12. The apparatus according to claim 11, further comprising a display configured to perform, when a plurality of the projected images has been generated, a multi-view display of the plurality of projected images.

13. A medical diagnostic imaging apparatus, comprising:

a contrast agent imaging apparatus configured to scan a three-dimensional region in a subject having a contrast agent injected therein over a predetermined period and acquire image data concerning the three-dimensional region over the predetermined period; and a computer configured, via programs stored on a non-transitory computer-readable medium, to:

generate first volume data in each time phase in an analysis period by using the image data concerning the three-dimensional region over the analysis period in the predetermined period and to generate second volume data indicative of contrast agent temporal information about the analysis period and third volume data indicative of a contrast agent characteristic amount at each position in the three-dimensional region in the analysis period, the second volume data and the third volume data being generated from the first volume data, wherein the contrast agent temporal information in the second volume data is one of a contrast agent arrival time for each voxel in the second volume data, a peak time at which a luminance value of the first volume data becomes a maximum value, a Wash-In time, and a Wash-Out time, and the contrast agent characteristic amount is one of a maximum value of the luminance value, a minimum value of the luminance value, and an average value of the luminance value;

determine a display color for each pixel in a projected image of the second volume data and the third volume data by:

assigning, to each position in the three-dimensional region by use of a color map, a color phase and a display attribute different from the color phase associated with the contrast agent temporal information and the contrast agent characteristic amount of each position respectively, determining a projection direction, determining, for each pixel in the projected image, a ray along the projection direction and identifying assignment results having positions that intersect the ray, projecting, for each pixel in the projected image, the identified assignment result along the ray, and determining a display color for each pixel based on the respective projections of the identified assignment results along respective rays; and generate the projected image using the determined display colors.

14. The apparatus according to claim 13, wherein the computer is further configured to:

calculate, for each ray of its respective projected image pixel, one of a variance value of the contrast agent temporal information having positions that intersect with the ray, a maximum value of the contrast agent temporal information having positions that intersect with the ray, a minimum value of the contrast agent temporal information having positions that intersect with the ray, and an average value of the contrast agent temporal information having positions that intersect with the ray by using the second volume data, and generate the projected image using the color map by assigning, to each pixel of the projection image, a color phase that differs depending on the respective calculated value.

15. The apparatus according to claim 13, wherein the computer is further configured to:

select, from the voxels of the third volume data intersected by each respective ray, a voxel having a maximum or minimum luminance value for each respective ray, specify a voxel in the second volume data associated with the selected voxel for each selected voxel respectively, and assign color phases to respective projected image pixels associated with respective rays that differ depending on respective contrast agent temporal information of the specified voxels.

16. The apparatus according to claim 13, wherein the computer is further configured to calculate:

a temporal change in luminance value at each position in the three-dimensional region by using the first volume data in each time phase in the analysis period, and one of the peak time, the Wash-In time, and the Wash-Out time by using the temporal change in the luminance value at each position in the three-dimensional region.

17. The apparatus according to claim 13, wherein the computer is further configured to:

set at least one projection range that is used when generating the projected image, and utilize the at least one set projection range to generate the at least one projected image.

18. The apparatus according to claim 17, further comprising a display configured to perform, when a plurality of the projected images has been generated, a multi-view display of the plurality of projected images.

19. A projected image generating method, comprising:

acquiring, with an ultrasonic probe, ultrasonic data of a three-dimensional region in a subject over a predetermined period by:

injecting the subject with a contrast agent, and scanning the three-dimensional region with ultrasonic waves over the predetermined period using the ultrasonic probe;

generating, with a computer, first volume data in each time phase in an analysis period by using the acquired ultrasonic data concerning the three-dimensional region over the analysis period in the predetermined period and utilizing the first volume data to generate second volume data indicative of contrast agent temporal information, of the injected contrast agent, about the analysis period and third volume data indicative of a contrast agent characteristic amount, of the injected contrast agent, at each position in the three-dimensional region in the analysis period, the second volume data and the third volume data being generated from the first volume data, wherein the contrast agent temporal information in the second volume data is one of a contrast agent arrival time for each voxel in the second volume data, a peak time at which a luminance value of the first volume data becomes a maximum value, a Wash-In time, and a Wash-Out time, and the contrast agent characteristic amount is one of a maximum value of the luminance value, a minimum value of the luminance value, and an average value of the luminance value;

determining, with the computer, a display color for each pixel in a projected image of the second volume data and the third volume data by:

assigning, to each position in the three-dimensional region by use of a color image, a color phase and a display attribute different from the color phase associated with the contrast agent temporal information and the contrast agent characteristic amount of each position respectively, determining a projection direction, determining, for each pixel in the projected image, a ray along the projection direction and identifying assignment results having positions that intersect the ray, projecting, for each pixel in the projected image, the identified assignment result along the ray, and determining a display color for each pixel based on the respective projections of the identified assignment results along respective rays; and generating, with the computer, the projected image using the determined display colors.

* * * * *